(12) United States Patent
Kubota (10) Patent No.: US 10,786,153 B2
(45) Date of Patent: Sep. 29, 2020

(54) OPHTHALMOLOGIC IMAGING APPARATUS (71) Applicant: TOPCON CORPORATION, Tokyo (JP)

(72) Inventor: Atsushi Kubota, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 157 days.

(21) Appl. No.: 16/080,019

(22) PCT Filed: Jan. 6, 2017

(86) PCT No.: PCT/JP2017/000310
§ 371 (c)(1),
(2) Date: Aug. 27, 2018

(87) PCT Pub. No.: WO2017/149928
PCT Pub. Date: Sep. 8, 2017

(65) Prior Publication Data
US 2019/0059720 A1 Feb. 28, 2019

(30) Foreign Application Priority Data
Feb. 29, 2016 (JP) .................. 2016-037152

(51) Int. Cl.
*A61B 3/14* (2006.01)
*A61B 3/113* (2006.01)
(Continued)

(52) U.S. Cl.
CPC .............. *A61B 3/14* (2013.01); *A61B 3/0025* (2013.01); *A61B 3/102* (2013.01); *A61B 3/113* (2013.01);
(Continued)

(58) Field of Classification Search
CPC ............ A16B 3/102; A16B 3/113; A16B 3/14
(Continued)

(56) References Cited

U.S. PATENT DOCUMENTS 7,517,085 B2 * 4/2009 Teiwes .................. A61B 3/113
351/209
2009/0005691 A1 1/2009 Huang et al.
(Continued)

FOREIGN PATENT DOCUMENTS

EP 2 932 888 A1 10/2015
JP 2010-110556 A 5/2010
(Continued)

OTHER PUBLICATIONS

Extended Search Report issued in European Application 17759400.9-1124 dated Oct. 29, 2019.
(Continued)

*Primary Examiner* — Zachary W Wilkes
(74) *Attorney, Agent, or Firm* — Xsensus LLP (57) ABSTRACT

An ophthalmologic imaging apparatus of an embodiment includes a data acquisition device, photographing device, a controller, and an error detector. The data acquisition device acquires data by scanning a subject's eye using optical coherence tomography. The photographing device photographs the subject's eye to obtain a front image. The controller controls the data acquisition device to perform a series of scans along a preset path group. The error detector detects an error based on a series of data acquired by the series of scans and two or more front images that include one or more front images obtained by photographing device corresponding to the series of scans.

15 Claims, 7 Drawing Sheets

(51) Int. Cl.
*A61B 3/00* (2006.01)
*A61B 3/10* (2006.01)
*G06T 7/00* (2017.01)

(52) U.S. Cl.
CPC .. *G06T 7/0012* (2013.01); *G06T 2207/10101* (2013.01); *G06T 2207/30041* (2013.01)

(58) Field of Classification Search
USPC .................................................. 351/209, 246
See application file for complete search history.

(56) References Cited

U.S. PATENT DOCUMENTS

| | | |
|---|---|---|
| 2011/0134392 A1 | 6/2011 | Iwase et al. |
| 2011/0211057 A1 | 9/2011 | Iwase et al. |
| 2011/0228221 A1 | 9/2011 | Hanebuchi et al. |
| 2011/0301455 A1 | 12/2011 | Numajiri et al. |
| 2012/0033181 A1 | 2/2012 | Koizumi et al. |
| 2012/0274783 A1 | 11/2012 | Ko et al. |
| 2013/0176532 A1 | 7/2013 | Sharma et al. |
| 2013/0216115 A1 | 8/2013 | Iwase et al. |
| 2013/0229622 A1 | 9/2013 | Murase et al. |
| 2013/0301008 A1 | 11/2013 | Srivastava et al. |
| 2014/0204338 A1 | 7/2014 | Murase et al. |
| 2014/0300864 A1 | 10/2014 | Fukuma et al. |
| 2014/0320809 A1 | 10/2014 | Fukuma et al. |
| 2015/0313468 A1 | 11/2015 | Okada et al. |

FOREIGN PATENT DOCUMENTS

| | | |
|---|---|---|
| JP | 2010-523286 A | 7/2010 |
| JP | 2010-201102 A | 9/2010 |
| JP | 2010-264225 A | 11/2010 |
| JP | 2011-120655 A | 6/2011 |
| JP | 2011-215134 A | 10/2011 |
| JP | 2011-254959 A | 12/2011 |
| JP | 2013-180125 A | 9/2013 |
| JP | 2014-512245 A | 5/2014 |
| JP | 2014-140488 A | 8/2014 |
| JP | 2014-200680 A | 10/2014 |
| JP | 2015-083248 A | 4/2015 |
| JP | 2015-515894 A | 6/2015 |

OTHER PUBLICATIONS

Notice of Reasons for Refusal issued in Japanese Application 2016-037152 dated Jan. 8, 2020.
English-language translation of International Search Report and Written Opinion for International Application No. PCT/JP2017/000310 dated Mar. 14, 2017.

* cited by examiner

OPHTHALMOLOGIC IMAGING APPARATUS

CROSS-REFERENCE TO RELATED APPLICATION

This application is a national stage (under 35 U.S.C. 371) of International Patent Application No. PCT/JP2017/000310, filed Jan. 6, 2012, claiming priority to Japanese Patent Application No. 2016-037152, filed Feb. 29, 2016, both of which are herein incorporated by reference in their entirety.

Embodiments described herein relate generally to an ophthalmologic imaging apparatus that images a subject's eye utilizing optical coherence tomography (OCT).

BACKGROUND

Diagnostic imaging serves an important role in the field of ophthalmology. In recent years, utilization of OCT has advanced. OCT is being used not only for acquiring B-mode images and three dimensional images of a subject's eye but also for acquiring front images (or enface images) such as C-mode images and shadowgrams. OCT is also utilized for acquiring images in which a specific site of the subject's eye is emphasized and acquiring functional information. For example, images in which retinal blood vessels and choroidal blood vessels are emphasized can be constructed based on time-series data acquired by OCT. Such images are referred to as angiograms. Further, it is also possible to determine blood flow information (e.g., blood flow velocity, blood flow amount) from phase information contained in time-series data acquired by OCT. These imaging techniques are disclosed in, for example, patent documents 1 to 3 listed below. Further, a technique of repeatedly scanning the same cross section to acquire a plurality of images and averaging these images to create low noise images is also known (see, for example, patent document 4).

The imaging techniques as described above requires the application of three dimensional scanning, repeated scanning, etc. Three dimensional scanning and repeated scanning take from several seconds to ten seconds, and take more time in some cases. Therefore, there is a possibility that the position of the subject's eye is shifted or blinking occurs during scanning. In view of such problems, tracking and rescanning are introduced. Tracking is a technique of monitoring movements of a subject's eye during scanning with a video camera and controlling the optical scanner in real time in accordance with the movements (see, for example, patent document 5). The rescanning is a technique of monitoring a subject's eye during scanning with a video camera and again scanning the scanned position at the timing at which the subject's eye moved significantly or when the blinking occurred (see, for example, patent document 6).

[PATENT DOCUMENT 1] Japanese Unexamined Patent Application Publication No. 2014-200680

[PATENT DOCUMENT 2] Japanese Unexamined Patent Application Publication (Translation of PCT Application) No. 2015-515894

[PATENT DOCUMENT 3] Japanese Unexamined Patent Application Publication (Translation of PCT Application) No. 2010-523286

[PATENT DOCUMENT 4] Japanese Unexamined Patent Application Publication No. 2011-120655

[PATENT DOCUMENT 5] Japanese Unexamined Patent Application Publication (Translation of PCT Application) No. 2014-512245

[PATENT DOCUMENT 6] Japanese Unexamined Patent Application Publication No. 2015-83248

In conventional tracking and rescanning, images obtained by a video camera are analyzed to detect movements and blinking of a subject's eye. On the other hand, owing to recent advances in OCT techniques, the repetition rate of OCT scan (e.g., the repetition rate of B-scan) has become considerably higher than the frame rate of a video camera. For example, the frame rate of the video camera is about 20 to 50 FPS (that is, the frame intervals are about 20 to 50 ms) while typical repetition intervals of B-scan are about 2 to 3 ms. Therefore, movements of the subject's eye which cannot be detected by the video camera may affect OCT images. Further, there are problems that it is impossible to specify a scan affected by such movements of the subject's eye, and that it takes time to specify the scan affected thereby. Although it is conceivable to shorten detection intervals of the movements of the subject's eye, it is not realistic because a very expensive imaging apparatus is required to do so.

SUMMARY

An object of the present invention is to provide an ophthalmologic imaging apparatus capable of acquiring highly accurate OCT images despite the occurrence of movements or blinking of a subject's eye.

An ophthalmologic imaging apparatus of an embodiment includes a data acquisition device, a photographing device, a controller, and an error detector. The data acquisition device acquires data by scanning a subject's eye using optical coherence tomography. The photographing device photographs the subject's eye to obtain a front image. The controller controls the data acquisition device to perform a series of scans along a preset path group. The error detector detects an error based on a series of data acquired by the series of scans and two or more front images that include one or more front images obtained by the photographing device corresponding to the series of scans.

DETAILED DESCRIPTION

Exemplary embodiments of the present invention will be described in detail with referring to the drawings. The embodiments are ophthalmologic imaging apparatuses having the function as an optical coherence tomography (OCT) apparatus and the function of acquiring front images of the subject's eye. The latter function can be realized by, for example, a fundus camera, a scanning laser ophthalmoscope (SLO), a slit lamp microscope, an ophthalmologic surgical microscope, or an anterior eye segment photographing camera. Hereinafter, an exemplary ophthalmologic imaging apparatus that is a combination of a swept source OCT apparatus and a fundus camera will be described; however, embodiments are not limited thereto.

<Configuration>

Figure 1:
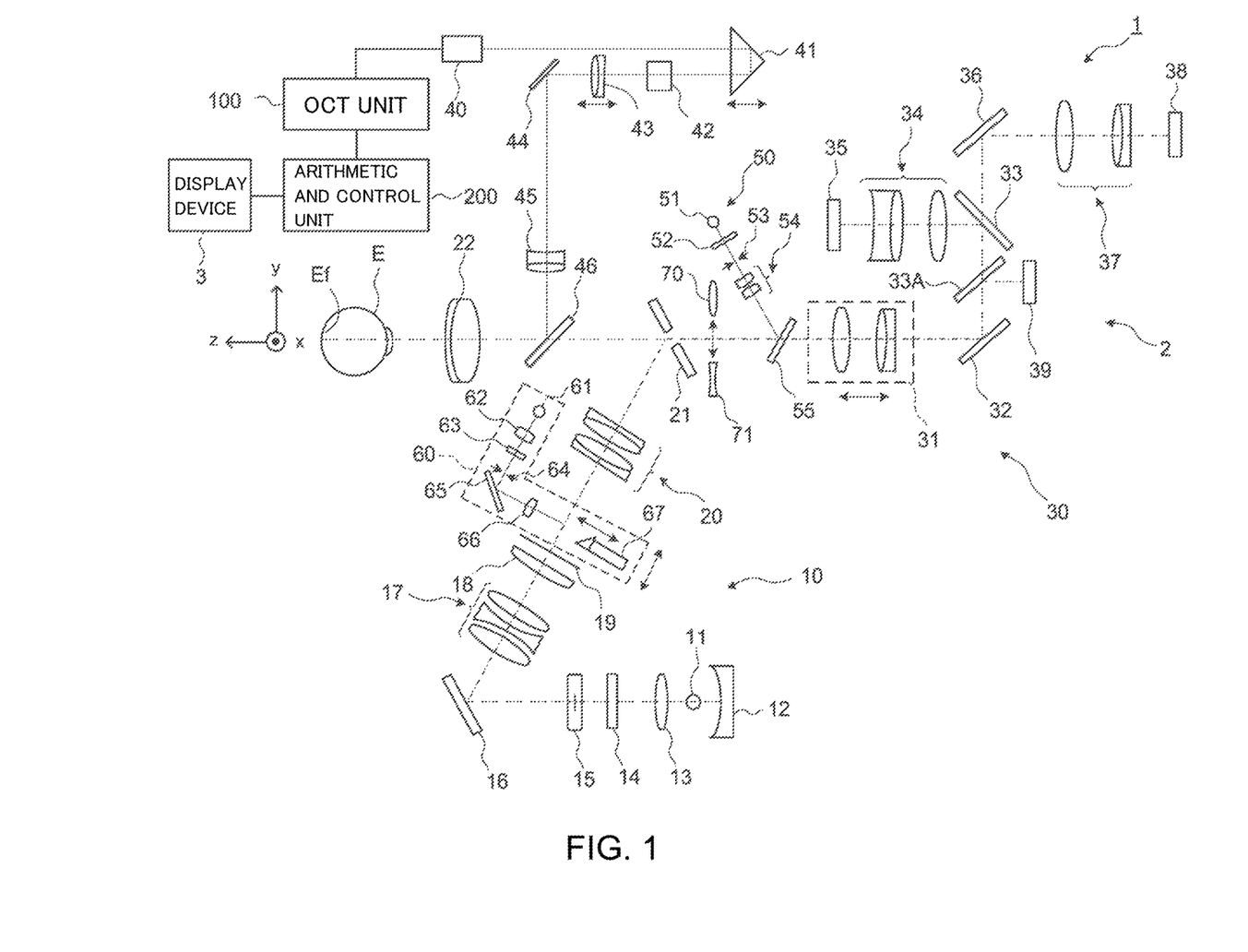
FIG. 1 is a schematic diagram illustrating an example of the configuration of an ophthalmologic imaging apparatus according to an embodiment.

As shown in FIG. 1, the ophthalmologic imaging apparatus 1 includes the fundus camera unit 2, the OCT unit 100 and the arithmetic and control unit 200. The fundus camera unit 2 is provided with an optical system and mechanism for acquiring front images of the subject's eye. The OCT unit 100 includes an optical system and a mechanism for performing OCT. The arithmetic and control unit 200 includes a processor that performs various calculations and controls. In addition to these, ophthalmologic imaging apparatus 1 may also include a member for supporting the face of the subject (e.g., a chin rest, a forehead rest) and a lens unit for switching the sites to be imaged by OCT (e.g., an attachment for an anterior eye segment OCT).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Images of fundus Ef (referred to as fundus images, fundus photographs, or the like) obtained include front images such as observation images and photographed images. An observation image is obtained by capturing a moving image using near-infrared light. A photographed image is a still image obtained by using flash light.

The fundus camera unit 2 includes the illumination optical system 10 and the photographing optical system 30. The illumination optical system 10 projects illumination light onto the subject's eye E. The photographing optical system 30 detects the returning light of the illumination light from the subject's eye E. The measurement light incident from the OCT unit 100 is directed to the subject's eye E through the optical path in the fundus camera unit 2, and the returning light thereof is directed to the OCT unit 100 through the same optical path.

The light output from the observation light source 11 of the illumination optical system 10 (called observation illumination light) is reflected by the reflection mirror 12 having a concave reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef or the anterior eye segment thereof). The returning light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the returning light passes through the half mirror 33A, is reflected by the dichroic mirror 33, and forms an image on the light receiving surface of the image sensor 35 by the condenser lens 34. The image sensor 35 detects the returning light at a predetermined frame rate. Note that the focus of the photographing optical system 30 is adjusted with respect to the fundus Ef or the anterior eye segment.

The light output from the photographing light source 15 (called photographing illumination light) passes through the same route as that of the observation illumination light and is projected onto the fundus Ef. The returning light of the photographing illumination light from the subject's eye E passes through the same route as that of the returning light of the observation illumination light, is guided to the dichroic mirror 33, passes through the dichroic mirror 33, is reflected by the mirror 36, and forms an image on the light receiving surface of the image sensor 38 by the condenser lens 37.

The LCD 39 displays a fixation target and a visual target used for visual acuity measurement. Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

The alignment optical system 50 generates an alignment indicator used for the alignment of the optical system with respect to the subject's eye E. The alignment light output from the LED 51 travels through the diaphragms 52 and 53 and the relay lens 54, is reflected by the dichroic mirror 55, and passes through the aperture part of the aperture mirror 21. The light having passed through the aperture part of the aperture mirror 21 penetrates the dichroic mirror 46 and is projected onto the subject's eye E by the objective lens 22. The cornea reflection light of the alignment light passes through the same route as that of the returning light of the observation illumination light and is guided to the image sensor 35. Based on the received image (called the alignment indicator image), manual alignment and/or automatic alignment can be performed.

The focus optical system 60 generates a split indicator used for the focus adjustment with respect to subject's eye E. The focus optical system 60 is moved along the optical path of the illumination optical system 10 (called the illumination optical path) in conjunction with the movement of the photography focusing lens 31 along the optical path of the photographing optical system 30 (called the photographing optical path). The reflection rod 67 can be inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef. The fundus reflection light of the focus light passes through the same route as the cornea reflection light of the alignment light and is guided to the image sensor 35. Based on the image (called the split indicator image), manual alignment and/or automatic alignment can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT. The dichroic mirror 46 reflects the light of wavelength bands used for OCT and transmits the light for fundus photography. Listed from the OCT unit 100 side, the collimator lens unit 40, the optical path length (OPL) changing device 41, the optical scanner 42, the OCT focusing lens 43, the mirror 44, and the relay lens 45 are placed in the optical path for OCT.

The optical path length changing device 41 is movable in the directions indicated by the arrow in FIG. 1 to change the optical path length for OCT. The change in the OCT optical path length can be utilized for correcting the optical path length according to the axial length, for adjusting the interference condition, and the like. The optical path length changing device 41 includes a corner cube and a mechanism for moving the corner cube.

The optical scanner 42 is placed at a position optically conjugate with the pupil of the subject's eye E. The optical scanner 42 deflects the measurement light LS that travels along the OCT optical path. The optical scanner 42 is, for example, a galvano scanner capable of two dimensional scanning.

The OCT focusing lens 43 is moved along the optical path of the measurement light LS in order to adjust the focus of the OCT optical system. The movement of the photography focusing lens 31, the movement of the focus optical system 60, and the movement of the OCT focusing lens 43 can be controlled in an interlocking manner.

<OCT Unit 100>

Figure 2:
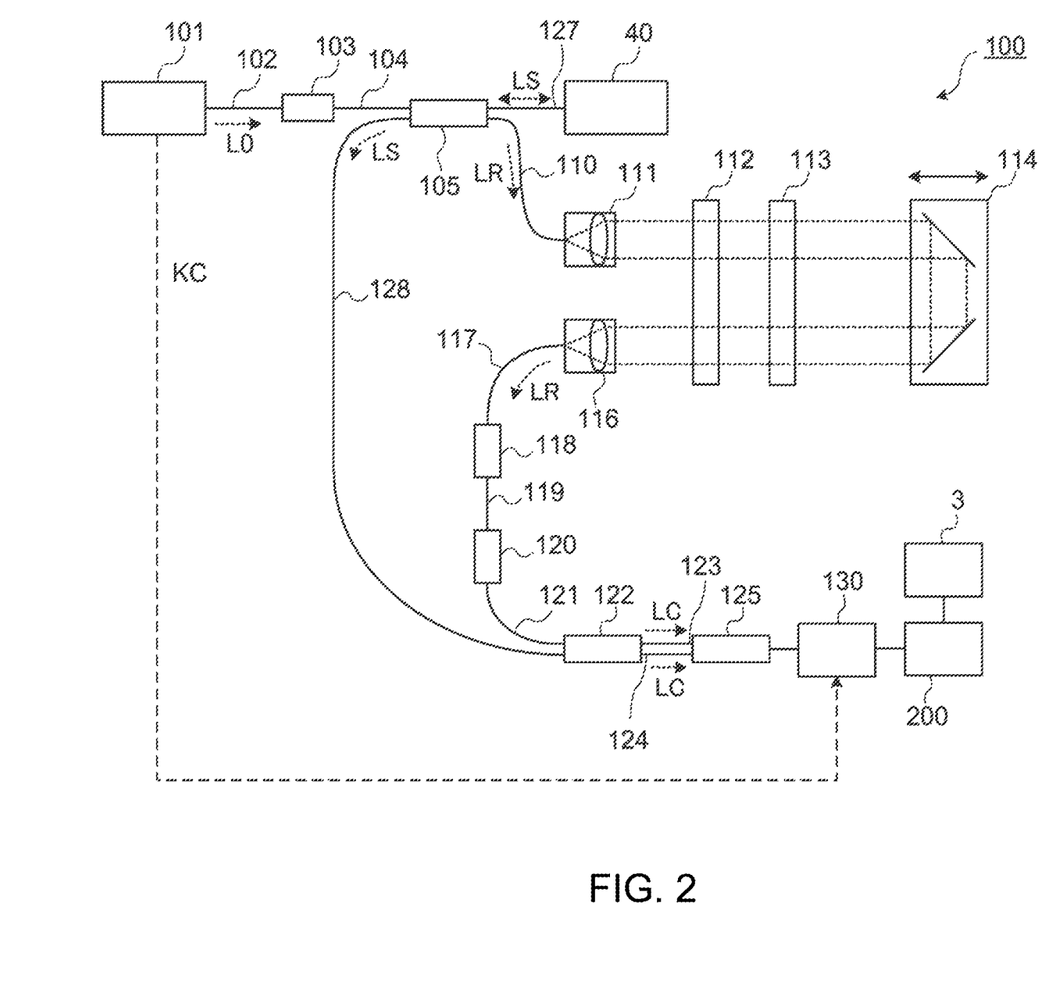
FIG. 2 is a schematic diagram illustrating an example of the configuration of the ophthalmologic imaging apparatus according to the embodiment.

As illustrated in FIG. 2, the OCT unit 100 is provided with the optical system for performing swept source OCT. The optical system includes an interference optical system. The interference optical system is configured to split the light emitted from the light source of wavelength tunable type (also called wavelength swept type) into measurement light and reference light, superpose the returning light of the measurement light from the subject's eye E and the reference light having traveled through the reference optical path to generate interference light, and detect the interference light. The detection result (i.e., detection signal) obtained by the interference optical system is a signal showing a spectrum of the interference light. The detection signal is sent to the arithmetic and control unit 200.

The light source unit 101 includes, for example, a near infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR.

The reference light LR is guided through the optical fiber 110 to the collimator 111, is converted into a parallel light beam, travels through the optical path length correction member 112 and the dispersion compensation member 113, and is guided to the corner cube 114. The optical path length correction member 112 acts to match the optical path length of the reference light LR and the optical path length of the measurement light LS with each other. The dispersion compensation member 113 acts to match the dispersion characteristics of the reference light LR and the dispersion characteristics of the measurement light LS with each other. The corner cube 114 is movable along the incident direction of the reference light LR. With this, the optical path length of the reference light LR is changed.

The reference light LR that has passed through the corner cube 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the optical path length changing device 41, the optical scanner 42, the OCT focusing lens 43, the mirror 44, and the relay lens 45, and then reaches the dichroic mirror 46. The measurement light LS is reflected by the dichroic mirror 46, is refracted by the objective lens 22, and is incident on the subject's eye E. The measurement light LS is reflected and scattered at various depth positions of the subject's eye E. The returning light of the measurement light LS from the subject's eye E travels along the same route as the outward way in the opposite direction, is directed to the fiber coupler 105, and then reaches the fiber coupler 122 via the optical fiber 128.

The fiber coupler 122 superposes (i.e., interferes) the measurement light LS incident through the optical fiber 128 and the reference light LR incident through the optical fiber 121 with each other, to generate interference light. The fiber coupler 122 splits the interference light at a predetermined splitting ratio (e.g., 1 to 1) to generate a pair of interference light LC. The pair of the interference light LC is guided to the detector 125 through the optical fibers 123 and 124, respectively.

The detector 125 is, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the DAQ 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, generate the combined light of the two pieces of split light, and generates the clock KC based on the result of the detection of the combined light. The DAQ 130 performs the sampling of the detection signal input from the detector 125 based on the clock KC. The DAQ 130 sends the result of the sampling of the detection signal from the detector 125 to the arithmetic and control unit 200.

The present example is provided with both the optical path length changing device 41 for changing the length of the optical path of the measurement light LS (called the measurement optical path or the measurement arm) and the corner cube 114 for changing the length of the optical path of the reference light LR (called the reference optical path or the reference arm). However, only one of the optical path length changing device 41 and the corner cube 114 may be provided. An optical member other than these may be employed to change the difference between the measurement optical path length and the reference optical path length.

<Control System>

Figure 3:
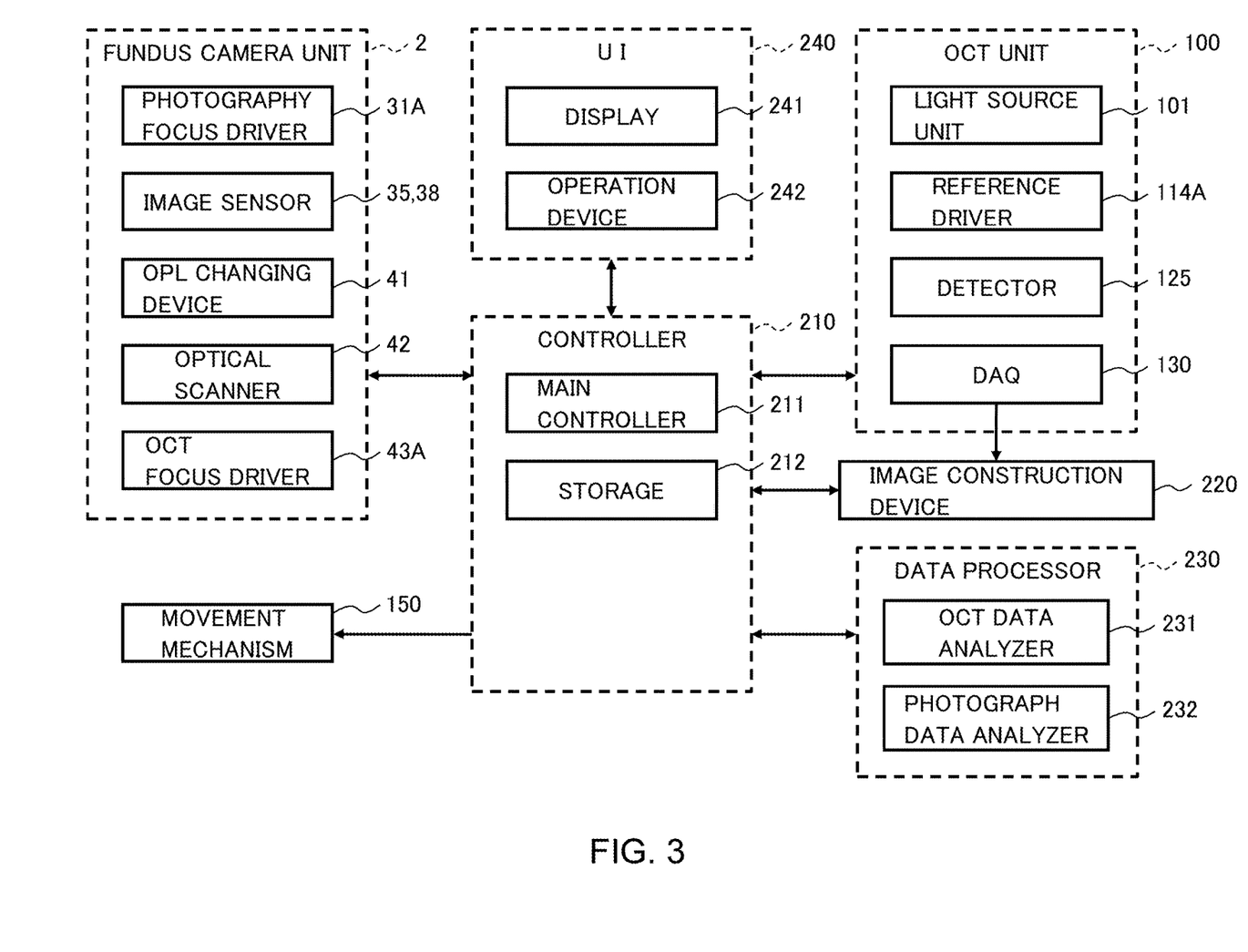
FIG. 3 is a schematic diagram illustrating an example of the configuration of the ophthalmologic imaging apparatus according to the embodiment.

FIG. 3 shows an example of the configuration of the control system of the ophthalmologic imaging apparatus 1. The controller 210, the image construction device 220 and the data processor 230 are provided in the arithmetic and control unit 200.

<Controller 210>

The controller 210 performs various kinds of controls. The controller 210 includes the main controller 211 and the storage 212.

<Main Controller 211>

The main controller 211 controls each part of the ophthalmologic imaging apparatus 1 (including the elements shown in FIG. 1 to FIG. 3). Note that the photography focus driver 31A shown in FIG. 3 moves the photography focusing lens 31, the OCT focus driver 43A moves the OCT focusing lens 43, the reference driver 114A moves the corner cube 114, and the movement mechanism 150 moves the fundus camera unit 2 in a three dimensional manner.

<Storage 212>

The storage 212 stores various kinds of data. Examples of the data stored in the storage 212 include OCT images, fundus images, and subject's eye information. The subject's eye information includes subject information such as the patient ID and the patient's name, identification information for the left eye and the right eye, and electronic medical record information.

<Image Construction Device 220>

The image construction device 220 constructs an image based on the output from the DAQ 130 (that is, based on the sampling result of detection signals). For example, as in the conventional swept source OCT, the image construction device 220 applies signal processing to the spectral distribution formed from the sampling result for each A-line to form the reflection intensity profile for each A-line. Then, the image construction device 220 creates a plurality of image data from the reflection intensity profiles for a plurality of A-lines and arranges the plurality of image data along a scan line. The aforementioned signal processing includes noise elimination (or noise reduction), filtering, and fast Fourier transform (FFT), for example.

<Data Processor 230>

The data processor 230 applies image processing and/or analysis to the image constructed by the image construction device 220. For example, the data processor 230 executes construction of three dimensional image data (e.g., stack data, volume data) from raster scan data, rendering of three dimensional image data, image correction, image analysis according to analysis application software. The data processor 230 includes the OCT data analyzer 231 and the photograph data analyzer 232.

<OCT Data Analyzer 231>

The OCT data analyzer 231 detects the occurrence of an error by analyzing a series of data acquired by a series of OCT scans (a "unit scan" to be described later) along a plurality of scan lines. The types of detectable errors include at least one of the shift (displacement, move) of the subject's eye E and the occurrence of blinking. The shift of the subject's eye E is, for example, fixation deviation. The types of the shift of the subject's eye E include at least one of a small shift and a large shift. Details of the processing executed by the OCT data analyzer 231 will be described later.

<Photograph Data Analyzer 232>

The photograph data analyzer 232 detects an error by analyzing two or more fundus images. The two or more fundus images include one or more fundus images acquired by the fundus camera unit 2 corresponding to a unit scan. The photograph data analyzer 232 detects, for example, the amount of an error whose occurrence has been detected by the OCT data analyzer 231. The photograph data analyzer 232 can also detects the occurrence of error. Details of the processing executed by the photograph data analyzer 232 will be described later.

<User Interface 240>

The user interface 240 includes the display 241 and the operation device 242. The display 241 includes the display device 3. The operation device 242 includes various kinds of operation devices and input devices. The user interface 240 may include a device, such as a touch panel, that has both the display function and the operation function. It is also possible to construct an embodiment that does not include at least part of the user interface 240. For example, the display device may be an external device connected to the ophthalmologic imaging apparatus.

<Scan Mode and Detection of Error>

The OCT scan mode that can be applied to the present embodiment and the processing that can be executed by the OCT data analyzer 231 and the photograph data analyzer 232 will be described.

Figure 4A:
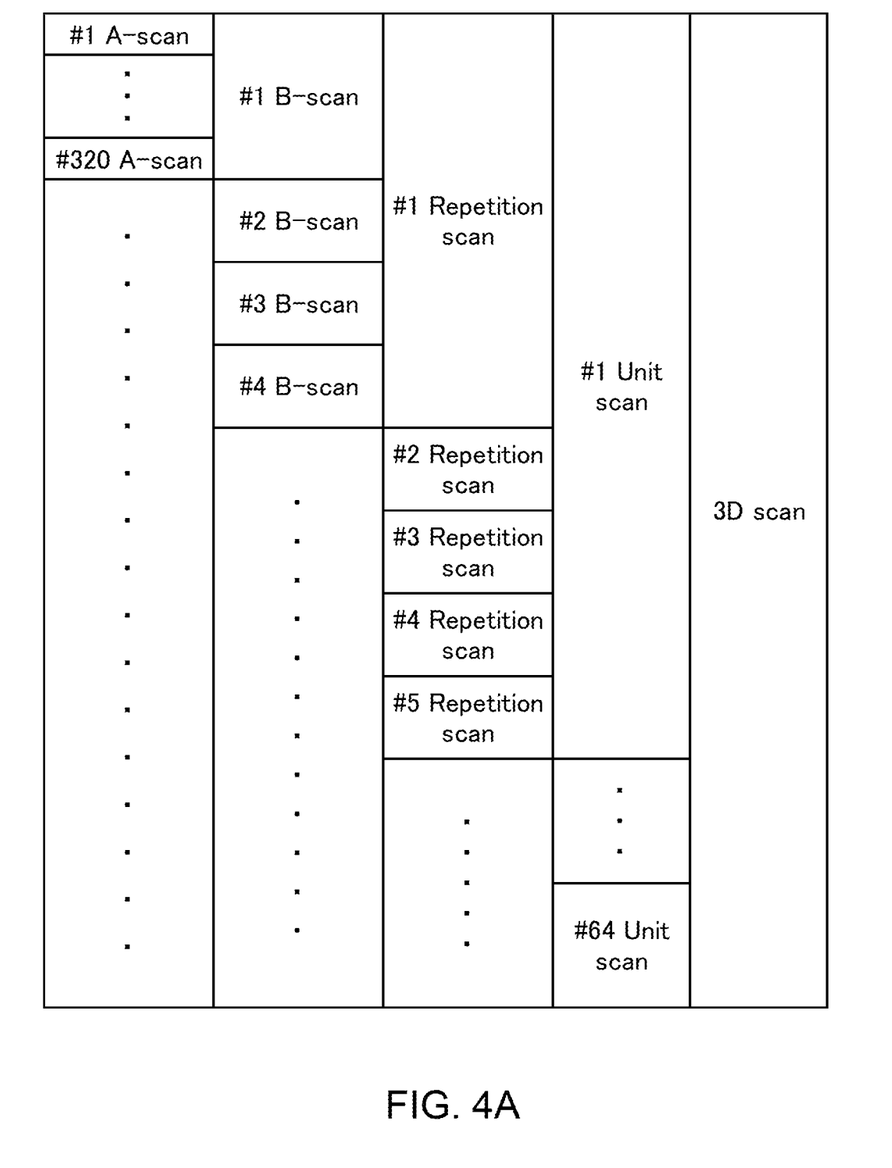
FIG. 4A is a schematic diagram illustrating an example of the operation of the ophthalmologic imaging apparatus according to the embodiment.

In the present example, a three dimensional scan (raster scan) is applied. The three dimensional scan is a scan along a plurality of mutually parallel scan lines. The three dimensional scan of the present example is shown in FIG. 4A and FIG. 4B.

Figure 4B:
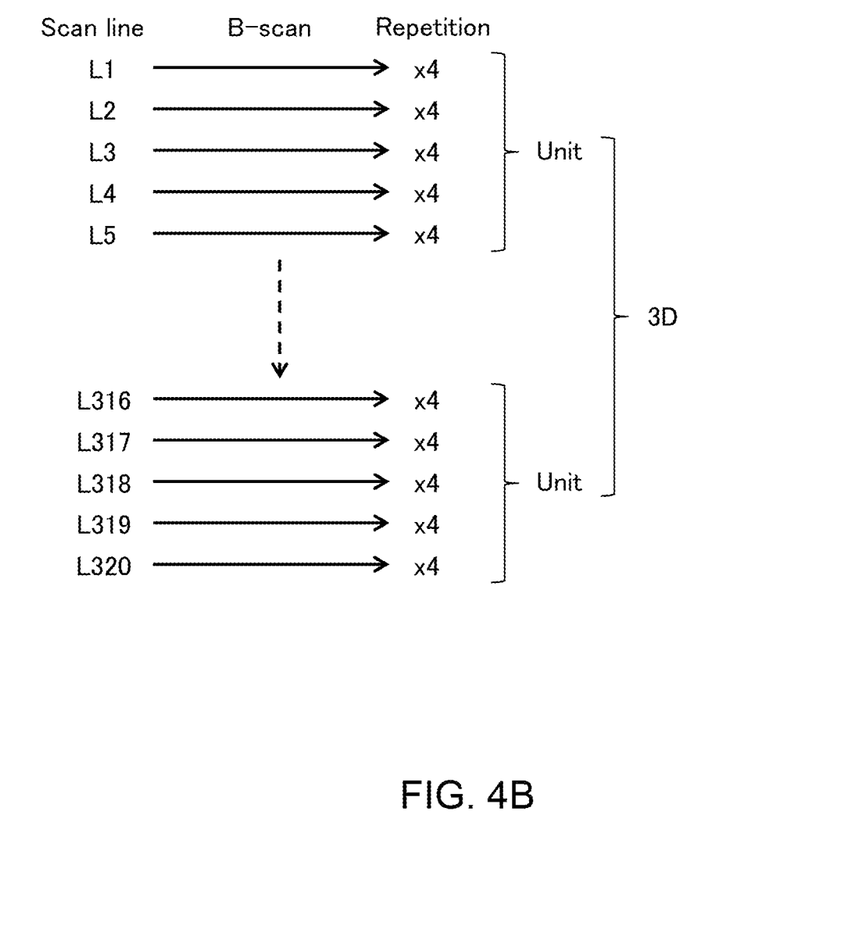
FIG. 4B is a schematic diagram illustrating an example of the operation of the ophthalmologic imaging apparatus according to the embodiment.

As shown in FIG. 4B, the three dimensional scan of the present example is performed for 320 scan lines L1 to L320. One scan along one scan line Li (i=1 to 320) is called a B-scan. One B-scan consists of 320 A-scans (see FIG. 4A). An A-scan is a scan for one A-line. That is, an A-scan is a scan for an A-line along the incident direction of the measurement light LS (i.e., along the z direction or the depth direction). A B-scan consists of 320 A-line scans arranged along a scan line Li on the xy plane orthogonal to the z direction.

In the three dimensional scan, the B-scans for the scan lines L1 to L320 are performed 4 times each in accordance with the arrangement order of the scan lines L1 to L320. 4 B-scans for each scan line Li is called a repetition scan. The scan lines L1 to L320 are classified into a plurality of sets each consisting of 5 lines, according to the arrangement order. The 64 sets obtained by the classification are called units, and scans for each unit are collectively called a unit scan. A unit scan consists of 4 B-scans for each of 5 scan lines. That is, a unit scan consists of a total of 20 B-scans.

The error detection process of the present example is executed for each unit. When no error has been detected during a three dimensional scan, 320×4×5×64 times of A-scans are performed in the temporal order shown in FIG. 4A and 4×5×64 number of B-scan images are acquired. On the other hand, when an error has been detected, a scan is performed again for the unit that has been under scanning when the occurrence of the error has been detected, as will be described later.

In the embodiment, for example, one of the following can be detected as an error.
(1) Blinking
(2) Relatively large fixation deviation (i.e., large shift of the subject's eye E)
(3) Relatively small fixation deviation (i.e., small shift of the subject's eye E)
(4) Incapability of determining the presence or absence of shift of the subject's eye E
(5) Amount of shift of the subject's eye E (including the shift direction)

(1) to (3) are detected on the basis of OCT data, and (4) and (5) are detected on the basis of a front image (fundus image). The present embodiment has the following advantages by combining OCT and fundus photographing. Firstly, in the conventional technique of detecting an error on the basis of an infrared fundus observation image, there has been a possibility (risk) to no small extent that omission (oversight) in detection will occur due to the slowness in the update frequency (i.e., slowness in frame rate). However, in the present embodiment, it is almost unlikely that omission in detection will occur because OCT with a fast update frequency (the repetition rate of B-scan) is utilized. Secondly, while the amount of shift of the subject's eye cannot be obtained with OCT alone, the present embodiment is capable of obtaining the amount of shift by analyzing front images and correcting scan positions. That is, the present embodiment can perform tracking. Thirdly, even when OCT data and a front image are simultaneously acquired at a certain timing, since a slight time difference actually exists between the acquisition of the OCT data and that of the front image, it is impossible to use an analysis result of one of the OCT data and the front image for confirmation of the other. On the other hand, the present embodiment is capable of detecting an error occurring during one unit scan by means of OCT and also detecting the amount of shift from front images obtained after the unit scan has started.

<Processing Executed by OCT Data Analyzer 231>

An example of processing executed by the OCT data analyzer 231 will be described.

As described above, the OCT data analyzer 231 detects occurrence of an error by analyzing a series of data (interference signals) acquired through each unit scan. The OCT data analyzer 231 analyzes each A-scan data (interference signal) included in each B-scan data and determines a characteristic value that represents a characteristic of the signal waveform thereof. The characteristic value is, for example, the number of characteristic points in the signal waveform. A characteristic point is, for example, a turning point (e.g., a point where an extreme value is taken, for example, a peak point which is convex upward) in the signal waveform, or a point where the amplitude is zero (a zero crossing). The OCT data analyzer 231 specifies characteristic points in A-scan data and counts the characteristic points. The OCT data analyzer 231 executes the above processing for each of 320 pieces of A-scan data included in a concerning B-scan data. With this, the 320 characteristic values are obtained for the B-scan. A set of the 320 characteristic values is referred to as characteristic information of the B-scan. Such processing is executed for each of 20 pieces of B-scan data obtained through a concerning unit scan. Thereby, 20 pieces of characteristic information are obtained for the unit scan. Furthermore, the OCT data analyzer 231 calculates a difference between two pieces of characteristic information and detects the presence or absence of an error based on the difference. The difference calculated here is, for example, a correlation coefficient or a mean square error.

(1) Detection of Blinking

For each scan line included in one unit scan, the OCT data analyzer 231 calculates correlation coefficients of a plurality of pairs of different combinations of 4 pieces of characteristic information based on repetition scan of a corresponding scan line. The plurality of pairs considered here are, for example, a pair of the first characteristic information and the second characteristic information, a pair of the second characteristic information and the third characteristic information, and a pair of the third characteristic information and the fourth characteristic information. The OCT data analyzer 231 determines whether or not the calculated correlation coefficient is less than a predetermined threshold value. If the correlation coefficient is less than the threshold value, the OCT data analyzer 231 determines that blinking has occurred during the repetition scan of the scan line.

In general, an interference signal acquired while blinking is occurring only contains noise components, and a correlation coefficient becomes almost zero. The detection of blinking described above is processing on the basis of such a phenomenon.

(2) Detection of Relatively Large Fixation Deviation

For each scan line included in one unit scan, the OCT data analyzer 231 calculates the mean square error of each of a plurality of pairs of different combinations of 4 pieces of characteristic information based on repetition scan of a corresponding scan line. The plurality of pairs considered here are, for example, all combinations of selecting 2 from the 4 pieces of characteristic information (C(4, 2)=6). The OCT data analyzer 231 determines whether or not the calculated mean square error error exceeds a predetermined threshold value. If the calculated mean square error error exceeds the predetermined threshold value, the OCT data analyzer 231 determines that the subject's eye E has shifted (that is, fixation deviation has occurred) during the repetition scan of the scan line.

A correlation coefficient can be calculated in place of a mean square error. Also, unlike the following detection process (3) which requires 20 pieces of B-scan data obtained by one unit scan, the detection process (2) uses only a part thereof. Therefore, the detection process (2) has an advantage that fixation deviation can be found at an early stage. The embodiment may be configured to execute only one of the detection processes (2) and (3).

(3) Detection of Relatively Small Fixation Deviation

For each scan line included in one unit scan, the OCT data analyzer 231 calculates the mean square error of each of a plurality of pairs of different combinations of 4 pieces of characteristic information based on the repetition scan of a corresponding scan line. The OCT data analyzer 231 then specifies the maximum value and the minimum value from among the plurality of mean square errors calculated for the plurality of pairs. The plurality of pairs considered here are all combinations of selecting 2 from the 4 pieces of characteristic information, for example.

The OCT data analyzer 231 specifies the maximum value and the minimum value from among the five maximum values and the five minimum values specified for the 5 scan lines corresponding to the concerning unit scan. The maximum value and the minimum value specified here are respectively the maximum value of the above five maximum values and the minimum value of the above five minimum values. The OCT data analyzer 231 calculates a difference between the maximum value and the minimum value corresponding to the unit scan and determines whether or not the difference exceeds a predetermined threshold value. If the difference exceeds the threshold value, the OCT data analyzer 231 determines that the subject's eye E has shifted (that is, fixation deviation has occurred) during the unit scan.

When fixation deviation has occurred during one B-scan of the repetition scans, the difference between the maximum value and the minimum value of the mean square error becomes large. On the other hand, when fixation deviation has occurred evenly, the difference between the maximum value and the minimum value becomes small. In the detection process (3), avoidance of omission in detection of error is attempted by comparing the mean square error corresponding to each repetition scan included in the unit scan.

The above example is configured to determine the maximum value of mean square errors by taking all pairs of combination of the 4 pieces of characteristic information (6 pairs) into account, but embodiments are not limited to this. For example, one (or more) of the 4 B-scans included in the repetition scan can be regarded as a scan for redundancy, and the maximum value can be determined by excluding a B-scan giving an outlier. The repetition scan is performed in an extremely short period of time, so it is considered that the cause of deteriorating the value of the mean square error is not fixation deviation but noise mixing. According to this modification, erroneous detection of an error due to noise mixing can be prevented.

<Processing Executed by Photograph Data Analyzer 232>

An example of processing executed by the photograph data analyzer 232 will be described. As described above, the photograph data analyzer 232 detects an error by analyzing two or more fundus images including one or more fundus images acquired, corresponding to the unit scan, by the fundus camera unit 2.

The two or more fundus images to be analyzed include at least one fundus image acquired during the period from the start to the end of the unit scan. In the present example, an infrared fundus observation image is acquired in parallel with the three dimensional scan described above. The infrared fundus observation image is a moving image with a predetermined frame rate. The frame rate is set so that at least one frame is captured during every single unit scan. That is, the frame rate of the infrared fundus observation image and the OCT scan conditions (e.g., the scan rate (scan repetition rate, scan frequency, scan repetition frequency), a total number of scan lines, the repetition number of repetition scans, the number of scan lines included in a unit scan) are set so that at least one frame is captured for every single unit scan.

The photograph data analyzer 232 analyzes two front images (that is, two frames of an infrared fundus observation image) acquired at different timings to calculate the amount of shift (including the direction of shift) of the fundus Ef depicted in these front images. In this analysis, for example, pattern matching such as a normalized correlation method or phase only correlation method (POC) is used as in conventional cases. One of the two frames to be compared is, for example, a reference image (a baseline image) acquired at the start of photographing (e.g., at the start of the OCT scan). In this case, the photograph data analyzer 232 calculates the amount of shift between a newly acquired front image (a frame acquired during a certain unit scan) and the reference image.

(4) Detection of Incapability of Determining the Presence or Absence of Fixation Deviation There are cases in which the amount of shift of the fundus Ef cannot be obtained, for example, when the areas of the fundus Ef depicted in the two front images are completely different or when at least one of the two front images is out of focus. In order to detect such an error, for example, the following processing can be executed. The photograph data analyzer 232 calculates the normalized correlation value between the newly acquired front image and the reference image. If the normalized correlation value is less than a predetermined threshold value, the photograph data analyzer 232 determines that an error has occurred.

Here, it is also possible to utilize an image of a different kind from an infrared fundus observation image. For example, phase images can be created and the correlation between the phase images can be utilized. Here, the phase images represent time-dependent changes in phase between a plurality of B-scan images obtained by a repetition scan. Further, a fundus image obtained by flashing visible light (e.g., the above-mentioned photographed image) or a fluorescence image can also be utilized.

The threshold value used for determining the magnitude of the correlation value may be set by any method. For example, the threshold value can be set taking into consideration a fact that a correlation value becomes low for a subject's eye where opacity is occurring due to cataract or another cause. Further, when errors are detected one after another a predetermined number of times in the detection process (4) (i.e., when a predetermined error condition is satisfied), the threshold value can be decreased in a continuous or stepwise manner.

(5) Detection of the Amount (Including the Direction) of Fixation Deviation

As described above, the photograph data analyzer 232 can calculate the amount of shift between two front images (i.e., the amount of shift of the subject's eye E). This processing is executed, for example, when occurrence of shift has been detected by the OCT data analyzer 231. With this, while detecting the occurrence of the shift on the basis of OCT data, the amount of the detected shift can be determined on the basis of infrared fundus observation image or another image.

The main controller 211 can feed the calculated amount of shift back to the OCT scan. For example, the storage 212 stores control information of the optical scanner 42 when the reference image has been acquired, and control information of the optical scanner 42 for each unit scan. The control information includes, for example, a group of coordinates corresponding to the B-scan. The main controller 211 can correct the control information with the amount of shift calculated by the photograph data analyzer 232 and can use the corrected control information to execute again the unit scan during which the shift has been detected. In addition, the amount of shift between the latest front image and the reference image can be calculated, and the control information can be corrected based on the calculated amount of shift to execute the unit scan. Further, it may be configure to detect an error by calculating the amount of shift between a front image corresponding to the unit scan and the reference image, and determining whether or not the difference between the amount of shift and the control information (the group of coordinates) is equal to or larger than a predetermined threshold value. The threshold value corresponding to, for example, 0.5 pixel. 0.7 pixel, or 1.0 pixel may be applied to this processing.

<Operation>

Figure 5:
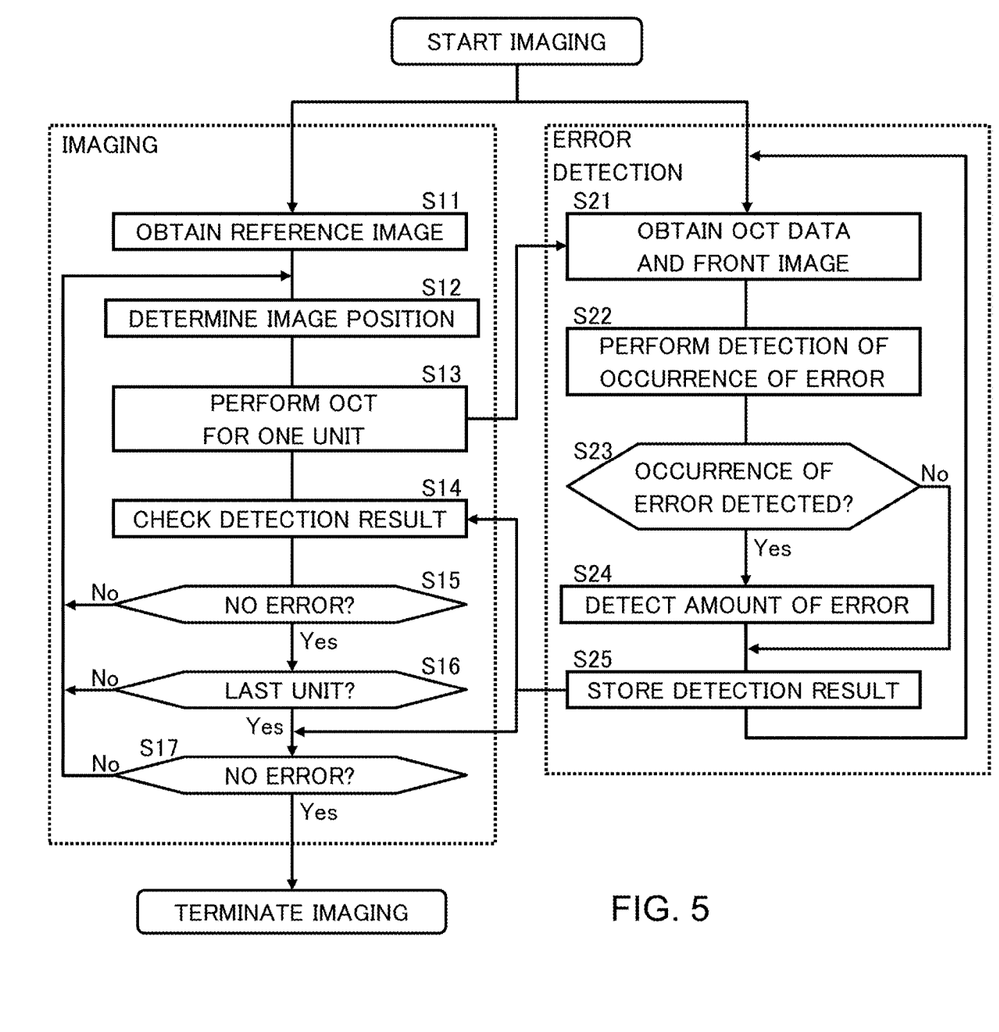
FIG. 5 is a flowchart illustrating an example of the operation of the ophthalmologic imaging apparatus according to the embodiment.

The operation of the ophthalmologic imaging apparatus 1 will be described. An example of the operation is shown in FIG. 5.

(Preparation for Imaging)

First, preparation for imaging is performed. The examiner activates the ophthalmologic imaging apparatus 1 and operates a key (such as an icon in a graphical user interface) for execution of three dimensional scan mentioned above. In response to this, the main controller 211 displays a screen for observing the fundus Ef with a live OCT image (moving OCT image) on the display 241. The examiner uses the operation device 242 (e.g., a joystick) to move the main body of the apparatus (e.g., the fundus camera unit 2) away from the chin rest, etc. With this, observation of the anterior eye segment becomes possible.

The subject is seated on a chair (not shown), the chin is placed on the chin rest, and the forehead is brought into contact with the forehead rest. The examiner adjusts the height of the chin rest etc. according to the sitting height of the subject. Upon receiving the predetermined operation, the main controller 211 turns on the observation light source 11, and controls the display 241 to display an observation image (an anterior eye segment observation image) based on the output from the image sensor 35. The examiner (or the ophthalmologic imaging apparatus 1) adjusts the position of the main body of the apparatus so that the pupil of the subject's eye E is displayed at the center of the frames of the observation image. When this position adjustment has been completed, the examiner (or the ophthalmologic imaging apparatus 1) brings the main body of the apparatus close to the subject's eye E. With this, the observation target is switched from the anterior eye segment to the fundus Ef, and the observation image of the fundus Ef is displayed on the display 241.

At this stage or before this stage, the main controller 211 controls the alignment optical system 50 to start the projection of the alignment indicator (two alignment bright spots). Two alignment bright spot images are depicted in the observation image. The examiner (or the ophthalmologic imaging apparatus 1) adjusts the position of the main body of the apparatus in such a manner that the two alignment bright spot images overlap with each other and are depicted within a target area (defined by brackets, for example) displayed at the center of the frames.

When this position adjustment has been completed, the optimization of various settings for performing OCT is executed. At this stage or before this stage, the main controller 211 controls the focus optical system 60 to start the projection of the split indicator. This optimization includes the optical path length adjustment (e.g., the adjustment of at least one of the position of the optical path length changing device 41 and the position of the corner cube 114), the polarization adjustment (e.g., the control of at least one of the polarization controllers 103 and 118), the light amount adjustment (e.g., the control of the attenuator 120), the focus adjustment (e.g., the adjustment of the position of the OCT focusing lens 43), and other adjustments.

After the completion of the optimization, the examiner (or the ophthalmologic imaging apparatus 1) checks whether or not problems such as flare mixing have occurred in the observation image. When it has been confirmed that no problem has occurred, the examiner performs an operation to start imaging using the operation device 242. Upon receiving the start of imaging issued by the examiner, the main controller 211 can overlay an image that represents the current scan position by OCT on the observation image.

(S11: Obtain Reference Image)

The main controller 211 registers a frame (i.e., a front image) of the observation image obtained at this stage as a reference image. The photograph data analyzer 232 starts the process of detecting the shift between the reference image and a frame acquired thereafter. In the case where the shift exceeds the threshold value or in the case where the detection of the shift has become impossible due to the influence of the blinking or fixation deviation, the main controller 211 registers a newly acquired frame as a new reference image.

When the reference image has been registered, the photograph data analyzer 232 sequentially calculates the shifts between frames acquired subsequently and the reference image. The main controller 211 corrects the orientation of the optical scanner 42 so as to cancel the shifts that are sequentially calculated. This processing may be executed in the same manner as the conventional tracking. The correction of the orientation of the optical scanner 42 is not executed while one repetition scan is being performed, but the correction is executed after the completion of the repetition scan.

The method and timing of the registration of a reference image are not limited to these. For example, it is possible to register a reference image by any method at any timing of the subsequent processes. Further, a reference image can be updated with any method and at any timing (under any condition).

(S12: Determine Imaging Position)

Figure 6:
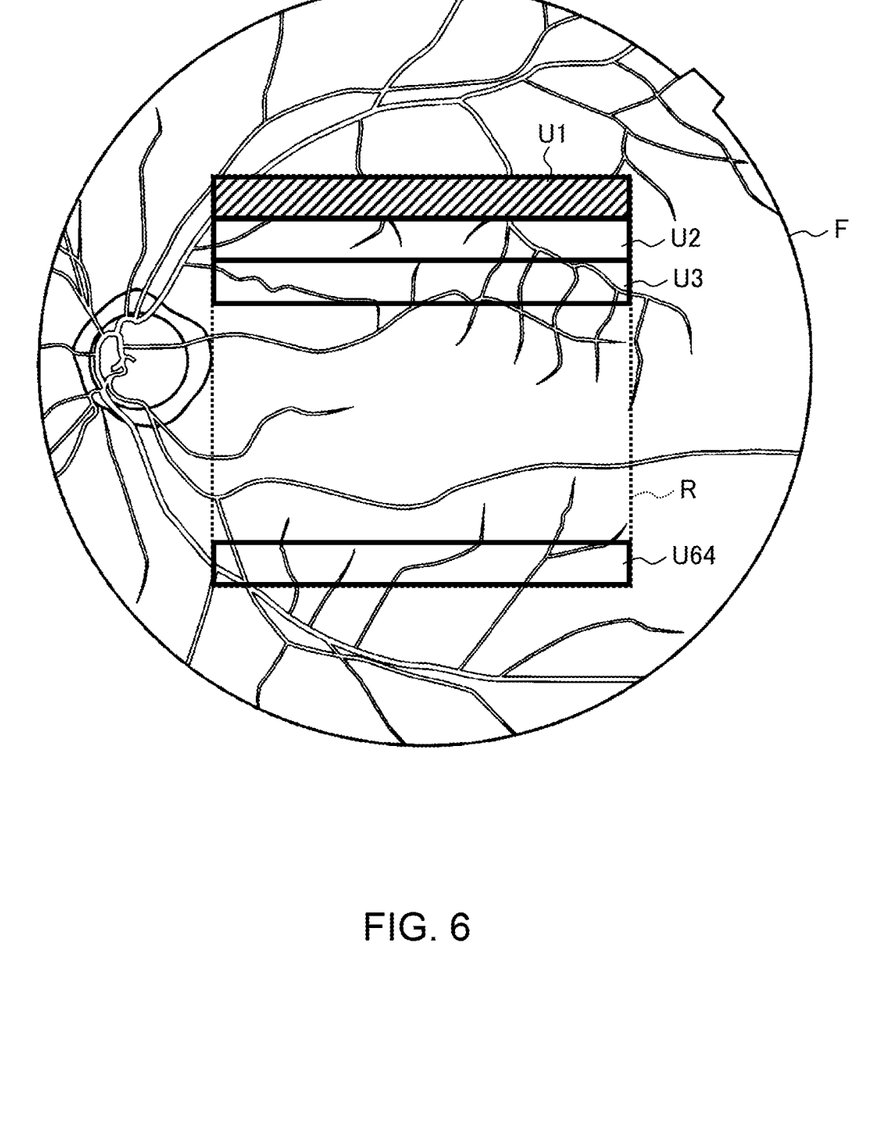
FIG. 6 is a schematic diagram for describing an example of the operation of the ophthalmologic imaging apparatus according to the embodiment.

The main controller 211 determines the position to which OCT scan is applied (imaging position). At the stage immediately after the start of the imaging, an area to which three dimensional scan is applied is set. Reference is now made to FIG. 6. The reference symbol F indicates a frame of an observation image, and the reference symbol R indicates a scan area of the three dimensional scan. Further, the scan area R is divided into 64 unit scan areas U 1 to U64. The unit scan areas U1 to U64 correspond to the unit scans "#1 Unit scan" to "#64 Unit scan" shown in FIG. 4A, respectively. Such a scan area R is set at the stage immediately after the start of the imaging.

(S13: Perform OCT for One Unit)

The main controller 211 executes OCT scan based on the imaging position determined in step S12. At the stage immediately after the start of the imaging, the three dimensional scan for the scan area R is started from the scan for the first unit scan area U (i.e., "#1 Unit scan" in FIG. 4A). Also, in parallel with OCT, the infrared moving image photographing of the fundus Ef is carried out at a predetermined frame rate.

(S21: Obtain OCT Data and Front Image)

The main controller 211 sends the data acquired by the OCT scan for one unit scan area in step S13 and a frame of the observation image acquired in parallel with the unit scan, to the data processor 230. Immediately after the start of the imaging, the data processor 230 obtains the OCT data of 20 B-scans acquired by the first unit scan for the first unit scan area U1 (i.e., "#1 Unit scan") and a frame of the observation image acquired in parallel with the first unit scan. Note that the OCT scan and the infrared moving image photographing started in step S13 are executed in parallel with the error detection in steps S21 to S25.

(S22: Perform Processing of Detecting Occurrence of Error)

The OCT data analyzer 231 executes a process for detecting occurrence of an error such as shift or blinking of the subject's eye E. For example, the OCT data analyzer 231 executes any of the above-described detection processes (1) to (3). In addition, the photograph data analyzer 232 executes, for example, the detection process (4) to detect occurrence of an error.

(S23: Has Occurrence of Error Detected?)

When occurrence of an error has not been detected in step S22 (S23: No), that is, when the ophthalmologic imaging apparatus 1 has determined that no error has occurred during the corresponding unit scan, the process proceeds to step S25. On the other hand, when an error occurred during the unit scan has been detected (S23: Yes), the process proceeds to step S24.

(S24: Detect Amount of Error)

When occurrence of an error has been detected in step S22 (S23: Yes), the photograph data analyzer 232 calculates the amount of shift (shift direction and shift amount) of the subject's eye E, for example, by performing the detection process (5). Then, the process proceeds to step S25.

The error detection processes in steps S22 to S24 are executed, for example, in the following manner. First, the detection process (1) is executed. Specifically, the OCT data analyzer 231 determines the aforementioned characteristic information based on the OCT data obtained in the first 4 B-scans of the corresponding unit scan and calculates their correlation coefficient. If the correlation coefficient is less than the threshold value, the OCT data analyzer 231 determines that an error has occurred. Then, the ophthalmologic imaging apparatus 1 skips the other processes for detecting the occurrence of an error, and the process proceeds to step S24.

When occurrence of an error has not been detected in the detection process (1), the process proceeds to the detection process (2). Specifically, the OCT data analyzer 231 calculates the mean square error of each of the six pairs of all combinations of the 4 pieces of characteristic information based on the repetition scan, and determines whether or not the mean square error exceeds the threshold value. If the mean square error exceeds the threshold value, the OCT data analyzer 231 determines that an error has occurred. Then, the ophthalmologic imaging apparatus 1 skips the other processes for detecting the occurrence of an error, and the process proceeds to step S24. At this time, the maximum value and the minimum value of the mean square errors are maintained.

When occurrence of an error has not been detected in the detection process (2), the detection processes (1) and (2) are executed for the 4 pieces of B-scan data corresponding to other scan lines included in the corresponding unit scan.

Upon completion of the detection processes (1) and (2) based on the OCT data for 20 B-scans obtained through the corresponding unit scan, the process proceeds to the detection process (3). Specifically, the OCT data analyzer 231 specifies the maximum value and the minimum value from among the five maximum values and the five minimum values specified for the 5 scan lines subjected to the corresponding unit scan, and calculates the difference between the maximum value and the minimum value specified. If the difference exceeds the threshold value, the OCT data analyzer 231 determines that an error has occurred. Then, the ophthalmologic imaging apparatus 1 skips the other processes for detecting the occurrence of an error, and the process proceeds to step S24.

When no error has been detected in any of the detection processes (1) to (3) and no reference image has been registered at this stage, the observation image (i.e., a frame thereof) captured at the timing corresponding to the last B-scan (20th B-scan) of the corresponding unit scan can be adopted as the reference image.

When no error has been detected in any of the detection processes (1) to (3), the process proceeds to the detection process (4). More specifically, the photograph data analyzer 232 applies the normalized correlation method or the phase only correlation method to each of the frames captured during the corresponding unit scan and the reference image, to detect occurrence of an error. Alternatively, the photograph data analyzer 232 detects occurrence of an error through calculation of correlation between phase images. When no error has been detected in any of the detection processes (1) to (4) (S23: No), the process proceeds to step S25.

When no error has been detected in any of the detection processes (1) to (4) and the shifts of a plurality of frames with respect to the reference image have been calculated, the following processes can be executed: calculating a difference between the calculated plurality of shifts; determining whether the calculated difference is deviated by an amount equal to or more than a threshold value (e.g., 0.5 pixels) in at least one of the x direction and the y direction (here, the amount of correction of the scan position by tracking can be taken into consideration); and if the difference has been determined to be equal to or more than the threshold value, it is determined that an error has occurred.

On the other hand, when an error has been detected in any of the above processes (S23: Yes), the process proceeds to step S24. In step S24, the detection process (5), for example, is executed. Specifically, the photograph data analyzer 232 calculates the amount of shift between a frame of the observation image and the reference image.

(S25: Store Detection Result)

The result of the error detection obtained by the data processor 230 is stored in the storage 212. When occurrence of an error has not been detected in step S22 (S23: No), information indicating that no error has been detected is stored as a detection result.

On the other hand, when occurrence of an error has been detected in step S22 (S23: Yes) and the amount of the error has been detected (S24), information indicating that an error has been detected, information indicating the type of the error detected, information indicating the amount of the error detected, and other information are stored as a detection result, for example.

(S14: Check Detection Result)

The main controller 211 checks (refers to) the detection result stored in step S25 and recognizes the presence or absence of error and the amount thereof.

(S15: No Error?)

When no error has been detected (S15: Yes), the process proceeds to step S16. On the other hand, when an error has been detected (S15: No), the process returns to step S12. Then, an imaging position is determined so as to return the scan position to the first position of the unit scan in which the error has been detected (S12). Further, the imaging position can be corrected to cancel the shift detected.

(S16: Is it Last Unit?)

When no error has been detected (S15: Yes) and the corresponding unit scan is the OCT scan of the last unit scan area U64 (S16: Yes), the process proceeds to step S17.

On the other hand, when the corresponding unit is not the OCT scan of the last unit scan area U64 (S16: No), the process returns to step S12. Then, the next unit scan area of the unit scan area of the corresponding unit scan (or the next unit scan area of the unit scan area in which the unit scan is currently being performed) is set as an imaging position (S12). At this time, the imaging position can be corrected to cancel the shift detected.

(S17: No Error?)

When the current unit scan is the OCT scan of the last unit scan area U64 (S16: Yes), the process proceeds to the present step S17. When an error has been detected in the last unit scan (i.e., "#64 Unit scan" shown in FIG. 4A) (S17: No), the process returns to step S12. Then, an imaging position is determined so as to return the scan position to the first position of the last unit scan (S12). Further, the imaging position can be corrected to cancel the shift detected.

On the other hand, when no error has been detected in the last unit scan (S17: Yes), the present imaging is terminated. According to such an imaging mode, while a plurality of unit scan areas U1 to U64 are sequentially scanned, when an error occurs, the scan can be performed again by returning to the unit scan area in which the error has occurred.

<Actions and Effects>

Actions and effects of the ophthalmologic imaging apparatus according to the embodiment will be described.

The ophthalmologic imaging apparatus of the embodiment includes a data acquisition device, a photographing device, a controller, and an error detector. The data acquisition device acquires data by scanning a subject's eye using optical coherence tomography (OCT). The data acquisition device includes, for example, the OCT unit 100 and elements in the fundus camera unit 2 that form the measurement optical path. The photographing device photographs the subject's eye to obtain a front image. The photographing device includes, for example, the illumination optical system 10 and the imaging optical system 30. The controller controls the data acquisition device to perform a series of scans along a preset path group (a preset group of paths). The controller includes, for example, the main controller 211. As the series of scans, the above embodiment performs a unit scan along the path group consisting of 5 scan lines. The error detector detects an error based on a series of data acquired by the series of scans and two or more front images that include one or more front images obtained by the photographing device corresponding to the series of scans. One of the two or more front images may be a reference image. The detection of an error may include at least one of the detection of occurrence of an error and the detection of the amount of an error.

According to the embodiment configured as described above, it is possible to detect a movement or blinking of the subject's eye by using OCT scans whose repetition rate is sufficiently higher than the frame rate of video cameras. Further, the movement and blinking of the subject's eye and the amount of movement of the subject's eye can be detected from the front images. Therefore, highly accurate OCT images can be acquired even when a movement or blinking of the subject's eye has occurred.

In the embodiment, the error detector may include a first error detector and a second error detector. The first error detector detects occurrence of an error based on the series of data acquired by the series of scans using OCT. The second error detector detects the amount of an error based on the two or more front images obtained by the photographing device. For example, the first error detector includes the OCT data analyzer 231, and the second error detector includes the photograph data analyzer 232. Furthermore, the ophthalmologic imaging apparatus 1 may be configured so that when occurrence of an error has been detected by the first error detector, the second error detector detects the amount of the error.

In the embodiment, the series of scans using OCT may include scans (repetition scan) that are performed a predetermined number of times each in a sequential manner for the path group. Further, the series of data may include a predetermined number of data sets corresponding to each path included in the path group. The data sets may be a plurality pieces of B-scan data obtained by the repetition scan of each scan line. In addition, the first error detector may be configured to determine characteristic information of each of the predetermined number of data sets, and to detect occurrence of an error based on the characteristic information.

In the embodiment, the first error detector may be configured to calculate an error (e.g., the mean square error) of each of a plurality of pairs of different combinations of the predetermined number of pieces of characteristic information, for each path of the path group. In addition, the first error detector may be configured to specify the maximum value and the minimum value from among a plurality of errors calculated. Further, the first error detector can determine that an error has occurred during performance of the series of scans if the difference between the maximum value and the minimum value selected from a plurality of maximum values and a plurality of minimum values specified for the path group exceeds a threshold value. The detection process (3) in the above embodiment is an example of this processing.

In the embodiment, the first error detector may be configured to calculate an error (e.g., the mean square error) of each of a plurality of pairs of different combinations of the predetermined number of pieces of characteristic information, for each path of the path group. Further, the first error detector can determine that an error has occurred during performance of scans for a corresponding path if the error calculated exceeds a threshold value. The detection process (2) in the above embodiment is an example of this processing.

In the embodiment, and the first error detector may be configured to calculate a correlation coefficient of a plurality of pairs of different combinations of the predetermined number of pieces of characteristic information for each path of the path group, and to determine that an error has occurred during performance of scans for a corresponding path if the correlation coefficient calculated is less than a threshold value. The detection process (1) in the above embodiment is an example of this processing.

In the embodiment, the first error detector may be configured to analyze, for each of the predetermined number of data sets described above (e.g., the plurality pieces of B-scan data obtained by the repetition scan of each scan line), each of a plurality of pieces of A-scan data included in a corresponding data set to determine a characteristic value that represents a characteristic of a signal waveform, and to determine the characteristic information based on a plurality of characteristic values determined. The characteristic value may be the number of characteristic points in the signal waveform. These characteristic points may be local extremal points or zero crossings.

In the embodiment, the second error detector may be configured to detect a shift between the two or more front images as the amount of an error. Furthermore, the second error detector can calculate a shift between the two or more front images using phase only correlation (POC).

In the embodiment, the error detector may include a third error detector that detects occurrence of an error based on the front images. The third error detector is configured to calculate a correlation coefficient between the two or more front images and to determine that an error (e.g., a shift of the subject's eye, deviation of the focal position) has occurred during performance of scans for a corresponding path if the correlation coefficient is less than a threshold value. The detection process (4) in the above embodiment is an example of this processing. The photograph data analyzer 232 is an example of the third error detector.

In the embodiment, when an error has been detected by the error detector, that is, when an error has occurred, or when the amount of an error is large, the controller can control the data acquisition device to perform again the series of scans being performed when this error has occurred. With this, it is possible to scan again the area being scanned at the time of occurrence of the error and perform data acquisition again.

In the embodiment, the controller may control the data acquisition device to perform a series of scans in a sequential manner for a plurality of path groups that has been set in advance. In this case, the error detector can perform the error detection described above for each path group. In the above embodiment, the error detection is carried out for every single unit scan area while performing the unit scans for the 64 unit scan areas in a sequential manner. This makes it possible to acquire highly an accurate three dimensional OCT image (e.g., volume data) even when a movement or blinking of the subject's eye has occurred.

The embodiment described above is only an example of the present invention. Those who intend to implement the present invention may apply any modification (e.g., omission, substitution, replacement, addition) within the scope of the gist of the present invention.

The invention claimed is:

1. An ophthalmologic imaging apparatus comprising:
a data acquisition device including an optical coherence tomography scanner that acquires data by scanning a subject's eye using optical coherence tomography;
an image sensor that photographs the subject's eye to obtain a front image;
a controller circuit configured that controls the data acquisition device to perform a series of scans along a preset path group; and
an error detector circuit that detects an error based on a series of data acquired by the series of scans and two or more front images that include one or more front images obtained by the image sensor corresponding to the series of scans, wherein
the path group includes a plurality of paths having mutually different positions,
the data acquisition device performs successive scans on the plurality of paths with a first rate,
the image sensor repetitively photographs the subject's eye to obtain two or more front images with a second rate that is slower than the first rate. and
the error detector circuit includes
a first error detector circuit that detects occurrence of a shift of the subject's eye based on a series of data acquired by the data acquisition device from the plurality of paths with the first rate, and
a second error detector circuit that detects an amount of the shift of the subject's eye based on the two or more front images acquired by the image sensor with the second rate.

2. The ophthalmologic imaging apparatus of claim 1, wherein when occurrence of an error has been detected by the first error detector circuit, the second error detector circuit detects an amount of the error.

3. The ophthalmologic imaging apparatus of claim 1, wherein
the series of scans comprise a plurality of scans that are performed a predetermined number of times each in a sequential manner for the path group,
the series of data comprises a predetermined number of data sets corresponding to each path of the path group, and
the first error detector circuit determines characteristic information of each of the predetermined number of data sets and detects occurrence of an error based on the characteristic information.

4. The ophthalmologic imaging apparatus of claim 3, wherein
the first error detector circuit calculates an error of each of a plurality of pairs of different combinations of a predetermined number of pieces of characteristic information for each path of the path group, specifies a maximum value and a minimum value from among a plurality of errors calculated, and
determines that an error has occurred during performance of the series of scans if a difference between a maximum value and a minimum value from among a plurality of maximum values and a plurality of minimum values specified for the path group exceeds a threshold value.

5. The ophthalmologic imaging apparatus of claim 3, wherein the first error detector circuit calculates an error of each of a plurality of pairs of different combinations of a predetermined number of pieces of characteristic information for each path of the path group, and determines that an error has occurred during performance of scans for a corresponding path if the error calculated exceeds a threshold value.

6. The ophthalmologic imaging apparatus of claim 3, wherein the first error detector circuit calculates a correlation coefficient of a plurality of pairs of different combinations of a predetermined number of pieces of characteristic information for each path of the path group, and determines that an error has occurred during performance of scans for a corresponding path if the correlation coefficient calculated is less than a threshold value.

7. The ophthalmologic imaging apparatus of claim 3, wherein the first error detector circuit analyzes, for each of the predetermined number of data sets, each of a plurality of pieces of A-scan data included in a corresponding data set to determine a characteristic value that represents a characteristic of a signal waveform, and determines the characteristic information based on a plurality of characteristic values determined.

8. The ophthalmologic imaging apparatus of claim 7, wherein the first error detector circuit determines a number of characteristic points in the signal waveform as the characteristic value.

9. The ophthalmologic imaging apparatus of claim 8, wherein the characteristic points are local extremal points.

10. The ophthalmologic imaging apparatus of claim 1, wherein the second error detector circuit detects a shift between the two or more front images as an amount of an error.

11. The ophthalmologic imaging apparatus of claim 10, wherein the second error detector circuit calculates a shift between the two or more front images using a phase only correlation method.

12. The ophthalmologic imaging apparatus of claim 1, wherein the error detector circuit comprises a third error detector circuit that calculates a correlation coefficient between the two or more front images and determines that an error has occurred during performance of scans for a corresponding path if the correlation coefficient is less than a threshold value.

13. The ophthalmologic imaging apparatus of claim 1, wherein when an error has been detected by the error detector circuit, the controller circuit controls the data acquisition device to perform a corresponding series of scans again.

14. The ophthalmologic imaging apparatus of claim 1, wherein
the controller circuit controls the data acquisition device to perform a series of scans in a sequential manner for a plurality of path groups preset, and
the error detector circuit performs detection of the error for each path group.

15. A method of operating an ophthalmologic imaging apparatus, the method comprising:
acquiring data by scanning a subject's eye using optical coherence tomography;
photographing the subject's eye to obtain a front image;
performing a series of scans along a preset path group including a plurality of paths having mutually different positions;
detecting an error based on a series of data acquired by the series of scans and two or more front images that include one or more front images obtained by the photographing corresponding to the series of scans;
performing successive scans on the plurality of paths with a first rate;
repetitively photographing the subject's eye to obtain two or more front images with a second rate that is slower than the first rate,
detecting occurrence of a shift of the subject's eye based on a series of data acquired by the performing successive scans on the plurality of paths with the first rate; and
detecting an amount of the shift of the subject's eye based on the two or more front images acquired by the repetitively photographing with the second rate.

* * * * *